US011587679B2

(12) United States Patent
Kozloski et al.

(10) Patent No.: US 11,587,679 B2
(45) Date of Patent: Feb. 21, 2023

(54) GENERATING COMPUTER MODELS FROM IMPLICITLY RELEVANT FEATURE SETS

(71) Applicant: International Business Machines Corporation, Armonk, NY (US)

(72) Inventors: James R. Kozloski, New Fairfield, CT (US); Paolo Di Achille, Medford, MA (US); Viatcheslav Gurev, Bedford Hills, NY (US); Jaimit Parikh, Brookfield, CT (US)

(73) Assignee: International Business Machines Corporation, Armonk, NY (US)

( * ) Notice: Subject to any disclaimer, the term of this patent is extended or adjusted under 35 U.S.C. 154(b) by 399 days.

(21) Appl. No.: 16/831,428

(22) Filed: Mar. 26, 2020

(65) Prior Publication Data

US 2021/0304891 A1    Sep. 30, 2021

(51) Int. Cl.
  *G16H 50/20* (2018.01)
  *G06N 20/00* (2019.01)
  *G16H 50/50* (2018.01)
(52) U.S. Cl.
  CPC ............. *G16H 50/20* (2018.01); *G06N 20/00* (2019.01); *G16H 50/50* (2018.01)
(58) Field of Classification Search
  CPC ..................................................... G16H 50/50
  See application file for complete search history.

(56) References Cited

U.S. PATENT DOCUMENTS 8,078,554 B2    12/2011 Fung et al.

2012/0041318 A1*  2/2012 Taylor .................. A61B 8/06
                                                           600/504

(Continued)

FOREIGN PATENT DOCUMENTS

WO    WO-2021160686 A1 *  8/2021

OTHER PUBLICATIONS

Doyle et al., Bridging Paradigms: Hybrid Mechanistic-Discriminative Predictive Models, Mar. 2013, IEEE Transactions on Biomedical Engineering, vol. 60, No. 3, 735-742 (Year: 2013).*

(Continued)

*Primary Examiner* — Evangeline Barr
*Assistant Examiner* — Karen A Hranek
(74) *Attorney, Agent, or Firm* — Stephen J. Walder, Jr.; Kristofer Haggerty

(57) ABSTRACT

Mechanisms are provided for training a hybrid machine learning (ML) computer model to simulate a biophysical system of a patient and predict patient classifications based on results of simulating the biophysical system. A mechanistic model is executed to generate a training dataset. A surrogate ML model is trained to replicate logic of the mechanistic computer model and generate patient feature outputs based on surrogate ML model input parameters. A transformation ML model is trained to transform patient feature outputs of the surrogate ML model into a distribution of patient features. A generative ML model is trained to encode samples from a uniform distribution of input patient data into mechanistic model parameter inputs that are coherent to the target distribution of patient features and are input to the surrogate ML model. Input patient data for a patient is processed through the ML models to predict a patient classification for the patient.

18 Claims, 6 Drawing Sheets

(56) References Cited

U.S. PATENT DOCUMENTS

| | | | |
|---|---|---|---|
| 2013/0197881 A1 | 8/2013 | Mansi et al. | |
| 2013/0197884 A1* | 8/2013 | Mansi | A61B 8/469 703/2 |
| 2015/0242589 A1* | 8/2015 | Neumann | G06F 17/18 703/2 |
| 2016/0220311 A1 | 8/2016 | Mansi et al. | |
| 2017/0161635 A1* | 6/2017 | Oono | G06N 7/005 |
| 2017/0185740 A1* | 6/2017 | Seegerer | A61B 6/5235 |
| 2017/0330075 A1* | 11/2017 | Tuysuzoglu | G16H 50/50 |
| 2018/0144243 A1* | 5/2018 | Hsieh | G06F 30/20 |
| 2018/0158552 A1 | 6/2018 | Liu et al. | |
| 2018/0336319 A1* | 11/2018 | Itu | G16B 25/00 |
| 2020/0342359 A1* | 10/2020 | Hu | G06N 20/10 |
| 2021/0035340 A1* | 2/2021 | Wang | G06N 20/00 |
| 2021/0390689 A1* | 12/2021 | Buckler | G06N 3/084 |

OTHER PUBLICATIONS

Anand et al., Semi-Supervised Kernel Mean Shift Clustering, Jun. 2014, IEEE Transactions on Pattern Analysis and Machine Intelligence, vol. 36, No. 6, 1201-1215 (Year: 2014).*

Alber et al., Integrating machine learning and multiscale modeling—perspectives, challenges, and opportunities in the biological, biomedical, and behavioral sciences, 2019, npj Digital Medicine 2:115 (Year: 2019).*

Davies et al., Fast Parameter Inference in a Biomechanical Model of the Left Ventricle using Statistical Emulation, May 2019, Journal of the Royal Statistical Society (Year: 2019).*

Kissas et al., Machine learning in cardiovascular flows modeling: Predicting arterial blood pressure from non-invasive 4D flow MRI data using physics-informed neural networks, Sep. 2019, Computer methods in applied mechanics and engineering, 358 (Year: 2019).*

Peng et al., Multiscale modeling meets machine learning: What can we learn?, Jan. 2020, arxiv.org (Year: 2020).*

Chen, Zhong et al., "Biophysical Modelling Predicts Ventricular Tachycardia Inducibility and Circuit Morphology: A Combined Clinical Validation and Computer Modelling Approach", Journal of Cardiovascular Electrophysiology, 27(7), 2016, 28 pages.

Delingette, Herve et al., "Personalization of Cardiac Motion and Contractility From Images Using Variational Data Assimilation", IEEE Transactions on Biomedical Engineering, vol. 59, No. 1, Jan. 2012, pp. 20-24.

Kayvanpour, Elham et al., "Towards Personalized Cardiology: Multi-Scale Modeling of the Failing Heart", PLoS One, 10(7) e0134869, Jul. 31, 2015, 18 pages.

Krueger, M.W. et al., "Towards Personalized Biophysical Models of Atrial Anatomy and Electrophysiology in Clinical Environments", Biomedical Engineering/Biomedizinische Technik, 57 (SI-1 Track-Q), 2012, p. 156.

Lorenz, JN et al., "Measurement of intraventricular pressure and cardiac performance in the intact closed-chest anesthetized mouse", Am J Physiol, 272 (3 Pt2): H1 137-46, Mar. 1997, Abstract, 2 pages.

Neumann, Dominik, "Robust Personalization of Cardiac Computation Models", Doctoral Disseration, Friedrich-Alexander-Universitat Erlangen-Nurnberg, Amberg, Germany, Jun. 24, 2019, 158 pages.

* cited by examiner

GENERATING COMPUTER MODELS FROM IMPLICITLY RELEVANT FEATURE SETS

BACKGROUND

The present application relates generally to an improved data processing apparatus and method, and more specifically to mechanisms for generating computer models from implicitly relevant feature sets. In some illustrative embodiments, the present application relates to an improved data processing apparatus and method having mechanisms for generating personalized biophysical models from implicitly relevant clinical feature sets.

Biophysical models are computer models that attempt to simulate a biological system using mathematical formulations of the physical characteristics of the biological system. Such biophysical models are often used to predict the influence of various biological and physical factors on complex systems. However, such biophysical models are often limited due to the large number of input parameters in these models that are not easily measurable.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system, for training a hybrid machine learning (ML) computer model to simulate a biophysical system of a patient and predict patient classifications based on results of simulating the biophysical system. The method comprises executing a mechanistic computer model on an input dataset to generate an output dataset. The input dataset and output dataset are combined to provide a training dataset for training a surrogate ML model. The method further comprises performing machine learning training of the surrogate ML model, based on the training dataset, to train the surrogate ML model to replicate logic of the mechanistic computer model as part of the surrogate ML model, and generate patient feature outputs based on surrogate ML model input parameters. In addition, the method comprises performing machine learning training of a transformation ML model to transform patient feature outputs of the surrogate ML model into a distribution of patient features. Moreover, the method comprises performing machine learning training of a generative ML model to train the generative ML model to encode samples from a uniform distribution of input patient data into mechanistic model parameter inputs that are input to the surrogate ML model. Additionally, the method comprises processing input patient data for a patient through the trained generative ML model, the trained surrogate ML model, and trained transformation ML model to generate a predicted patient classification for the patient.

In one illustrative embodiment, training the generative ML model comprises performing a transfer learning operation based on a loss calculation for one or more downstream ML models that are downstream in a data flow from the generative ML model to the one or more downstream ML models. In some illustrative embodiments, the one or more downstream ML models comprises one or more of the surrogate ML model, the transformation ML model, or a prior ML model, wherein the prior ML model transforms a prior distribution to a uniform distribution. In some illustrative embodiments, the loss calculation for the one or more downstream ML models comprises a uniformity test based loss calculation on output of the one or more downstream ML models. In still other illustrative embodiments, the loss calculation for the one or more downstream ML models comprises a first loss calculation for the transformation ML model and a second loss calculation for the prior ML model, and the generative ML model is trained to encode samples based on both the first loss calculation and the second loss calculation.

In some illustrative embodiments, training the generative ML model comprises training the generative ML model as part of an identity transformation comprising a chain of transformations comprising a first transformation, by the generative ML model, from random samples of the uniform distribution of input patient data to mechanistic model parameters, a second transformation from mechanistic model parameters input to the surrogate ML model to outputs of a mechanistic model represented as the patient feature outputs that are output by the trained surrogate ML model, and a third transformation, by the transformation ML model, from the mechanistic model outputs to observed patient features.

In some illustrative embodiments, the surrogate ML model comprises one or more hidden layers of neurons that learn hidden patient pathophysiological states that are not able to be measured non-invasively. The hidden patient pathophysiological states may be represented in the surrogate ML model as one or more of indices or biomarkers calculated as functions of mechanistic model parameters.

The surrogate ML model, in some illustrative embodiments, models a mechanistic biological system of the patient. In some illustrative embodiments, the surrogate ML model models a cardiac system of the patient and wherein the surrogate ML model input parameters that are input to the surrogate ML model comprise heart geometry parameters of the patient.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
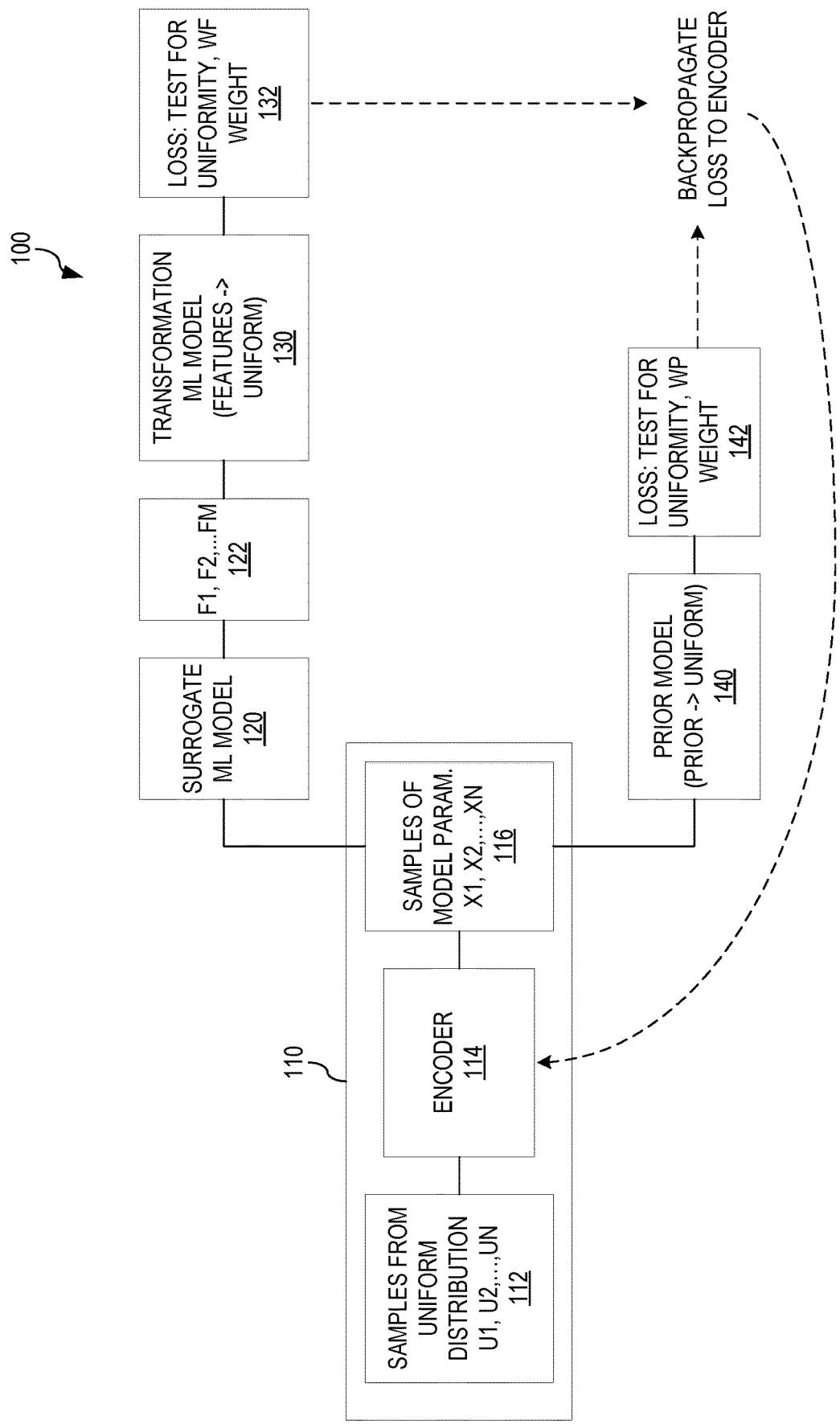
FIG. 1 is an example block diagram of a hybrid model architecture in accordance with one illustrative embodiment.

The illustrative embodiments described herein provide mechanisms implemented in specifically configured improved computing tools for automatically generating computer models from implicitly relevant feature sets. For example, the illustrative embodiments provide mechanisms for generating biophysical computer models that model the biological systems of a patient, while providing quantification about the model hidden biological metrics that are impractical to measure non-invasively, based on explicitly, as well as implicitly, relevant clinical feature sets that may be represented in patient electronic medical records. The illustrative embodiments provide mechanisms that implement a multi-model machine learning approach in which gradients of posterior probability densities with respect to parameters of the models are calculated by transfer from model-to-model in a back propagation manner enforcing sampling from given distributions of clinical feature sets. In so doing, an encoder model is trained to generate samples of biological metrics from a random variable with uniform distribution based on explicitly and implicitly relevant clinical patient data in patient electronic medical records, that correspond to distributions of actual real-world occurrences of such biological metrics. In this way, measurable clinical patient data may be used as a basis for generating realistic hidden biological metrics for modeling the biological systems of a patient.

It should be appreciated that while the principle embodiments described herein will be directed to computer modeling of biological systems, the invention is not limited to such. To the contrary, the present invention is applicable to any environment in which computer modeling of hidden metrics that are difficult or impossible to measure using non-invasive instrumentation may be approximated by machine learning based on implicitly relevant non-invasively measurable metrics. For example, illustrative embodiments may be applied to characterizing latent metrics in sociology, economics and other fields where mechanistic models and statistical models may be combined to make new predictions and to describe interactions of relevant variables.

Clinical patient data provides detailed information relevant to constructing a personalized medical state for diagnosis, prognosis, and determining a course of treatment. In the case of cardiology, for example, this data can inform general states, such as quality of life, heart disease progression, and the like, as well as specific states such as heart contraction efficiency, for example. However, standard clinical practices force doctors to reduce available patient data (such as imaging datasets, blood pressure, etc.) into succinct low-dimensional reports of standard features of interest in order for a doctor to infer detailed specific states about patient pathophysiology (the study of the changes of normal mechanical, physical, and biochemical functions caused by a disease or abnormal syndrome) that underlie the general states described by the patient's medical record. It is therefore up to clinicians to mentally build an interpretation of the patient's condition by combining their own detailed knowledge of biology and physiology with high level medical record data, i.e. high level clinical patient data.

Biophysical computer models of disease progression and aging have recently been developed. It should be appreciated that the terms "computer model" and "model" are used herein interchangeably to reference a combination of computer executable logic and stored data that together simulates or emulates a real world system, such as a biological system. For example, in some illustrative embodiments, a machine learning computer model or machine learning model, such as a neural network, for example, uses machine learning techniques to simulate or emulate a decision making or thought process that a physician, clinician, or other medical professional may perform intuitively, but instead using a different computer process performing a different set of computer specific operations. A mechanistic computer model, as discussed hereafter, is a static computer model that simulates a mechanical system, or in the case of some of the illustrative embodiments set forth herein, the mechanics, physics, and/or chemistry of a biological system. Such mechanistic computer models are composed of a fixed set of rules, equations, etc. that operate on input data. An example of a mechanistic computer model is the biophysical computer models mentioned above which simulates a biological system using fixed mathematical formulations of the physical properties of that system to thereby predict the influence of biological and physical factors on complex systems.

While biophysical computer models of disease progression and aging have been devised, these biophysical computer models have yet to find direct applications in clinical practice. The main obstacle to their adoption has been that these biophysical computer models are not accurate, as they consist of large number of hidden biological metrics/input parameters, or do not properly take into account the influence of key hidden biological metrics, that are not known and/or are highly variable among the subjects of biological system, e.g., cell population of individuals in population dynamics models. That is, these "hidden" biological metrics are metrics that cannot be measured without invasive instrumentation. In some cases, hidden parameters of the biological system are not possible to be measured at all within the biological system itself. As a result, doctors do not acquire such hidden biological metrics routinely due to the impracticability of their measurement. However, such key hidden biological metrics are necessary to inform and train accurate biophysical computer models such that they may accurately reproduce patient health states. That is, overall, there is a mismatch between clinical health metrics, i.e. metrics that a clinician may obtain non-invasively and record as clinical data in a patient electronic medical record, that are easily measurable from patients, e.g., peripheral blood pressure, electrocardiogram (ECG) data, and the like, and hidden health metrics, only obtainable from invasive instrumentation or not able to be obtained at all using known instrumentation techniques, that are necessary to gain actual biophysical insights on patient conditions, e.g., intraventricular pressure, myocardial strains, etc.

In order for a clinician to gain valuable insights into patient conditions, it is important that the clinician be able to identify pathophysiological reasons for the patient's condition. However, such information does not generally appear in low-dimensional, high level patient electronic medical records where standard features are only reported, e.g., blood pressure, ECG, etc. For example, a patient's electronic medical record does not document the intraventricular pressure as this requires invasive medical procedures to measure, such as introducing of polyethylene catheters into the artery and vein and a transducer in a ventricle, which is not done on human patients due to its invasiveness but has been done in a research capacity on mice (see Lorenz et al., "Measurement of Intraventricular Pressure and Cardiac Performance in the Intact Closed-Chest Anesthetized Mouse," Am J Physiol, 1997). Another example of hidden pathophysiological metrics that are not available to clinician without invasive measurements is pulmonic arterial pressure which is important to identify patients with heart failure. As a result of this lack of such information being present in patient medical records, patient medical records comprising clinical data do not provide a sufficient basis for training machine learning models that can accurately predict patient medical conditions, where such medical conditions are due to hidden pathophysiological parameters.

The illustrative embodiments described herein provide mechanisms for automating the construction of interpretative biophysical models by generating representations of hidden pathophysiological metrics based only on the general patient data, e.g., clinical data, described by a patient electronic medical record. Using a machine learning process, the illustrative embodiments assemble two computer models into a hybrid computer model solution. The hybrid computer model solution melds a mechanistic model approach that associates patient state, including diagnosis, prognosis, and disease progression, with patient data, and a machine learning model approach which implements a machine learning based pathophysiological computer model to predict pathophysiological outputs from pathophysiological computer model input parameters. These models facilitate the construction and training of a hybrid computing system which is able to predict biophysical parameters of a mechanistic model from patient data and thereby infer hidden biophysical metrics regarding cell and tissue pathophysiology and multi-scale biophysical effects from high level clinical data.

In addition, the illustrative embodiments provide a training mechanism and methodology for training the hybrid computing system using an abstraction layer which interprets relevant clinical phenotypes (observable characteristics of a patient resulting from an interaction of the patient's genotype (genetic constitution) with an environment) from tangentially relevant and general clinical data, such as may be provided in patient electronic medical records, based on hidden causal links, correlation, and/or mutual information with the modeled biophysical mechanisms. In this way, the illustrative embodiments modulate the generated illustration by leveraging data that may be related to the biophysical process of interest, allowing the mechanisms of the illustrative embodiments to inform clinicians automatically of likely interpretations of underlying pathophysiology given diagnostic features that may be overlooked in standard clinical feature sets as relevant to disease.

The mechanisms of the illustrative embodiments are designed to construct a generative model, also referred to as a generator or encoder, that transforms a random variable with normal or uniform distribution, to mechanistic model parameters with a distribution that is coherent with a feature set obtained from real world observations and constrained by the "prior" information, i.e. given or learned constraints, on the mechanistic model parameters. For example, a generator or encoder, which may be a machine learning model, is constructed that transforms a random variable $U1$, $U2, \ldots Un$, with normal or uniform distribution to a distribution of mechanistic model parameters $X1, X2, \ldots Xn$, e.g., parameters describing heart geometry, conductance of ion channels, rates of physiological processes in a cell, etc., which are coherent with a feature set $F1, F2, \ldots Fm$, e.g., blood pressure, electrocardiogram (ECG) signal, cardiac output, blood sugar levels, etc., which are features that may be obtained from real world observations and which are constrained by the "prior" information on the mechanistic model parameters, where again a "prior" is a given or learned constraint. The random variables $U1, U2, \ldots Un$ are auxiliary random variables that have no physical meaning, but which can be easily sampled from their distribution as the distribution is a basic distribution (uniform or Gaussian, for example).

The mechanisms for training the generative model depend on whether the mechanistic model is represented by an invertible transformation. If the mechanistic model is invertible, the generative model, i.e. generator or encoder, is trained as a part of identity transformation for the feature set obtained from real world observations. The identity transformation is represented as a chain of transformations from the observed features to mechanistic model parameters $X1, X2, \ldots Xn$, from model parameters $X1, X2, \ldots Xn$ to the mechanistic model output $F1, F2, \ldots Fm$, and from the mechanistic model output $F1, F2, \ldots Fm$ to the observed features $PF1, PF2, \ldots PFn$ (e.g., see FIG. 4 described hereafter). The mechanistic model is represented by a surrogate machine learning model to speed up calculations and to make it possible to calculate a gradient of the machine learning model output with respect to the machine learning model input. Stochastic gradient descent and backpropagation algorithms may be employed to optimize parameters of the transformations performed by the surrogate model to enforce identity (can replace one with the other).

In the case where the mechanistic model is not representable as an invertible transformation, the distributions of mechanistic model parameters are additionally constrained by a given "prior" information, i.e. given or learned constraints. To train the generative model, or generator/encoder, a machine learning (ML) model is constructed which is composed of several components (e.g., see FIGS. 1 and 3 described hereafter). These components include the generative model, or generator/encoder, transformations of samples, from prior parameter and observed feature distributions, to samples from the normal or uniform distributions, and loss functions that enforce distributions to be normal or uniform at the output of the ML model. In some illustrative embodiments, transformations of "prior" and feature distributions to normal or uniform distributions are constructed and trained as Masked Autoregressive Flow or non-deterministic transformations based on mixture models, however, other techniques and loss functions are possible, e.g., based on optimization of likelihood or infomax principle.

In one illustrative embodiment, the ML model is trained on mini-batches of samples from uniform or normal distributions that are fed to a root of the component tree, i.e. the data flow tree comprising components including the various machine learning models and other logic described herein.

In one illustrative embodiment, the parameters of the ML model are optimized by Stochastic Gradient Descent using a backpropagation algorithm, or other suitable machine learning optimization technique, that operates to minimizes one or more loss functions that enforce uniform or normal distributions. In some illustrative embodiments, two loss functions bias the generated distribution of model parameters to the given "prior" (constraint) and to the distribution coherent with distribution of observable features. The weights of the loss function(s) are calibrated to balance between coherency of generated model parameters with distributions of observed feature sets and closeness of the parameter distribution to the "prior" (constraint).

In some cases, clinical features do not belong either to the input or output space of the mechanistic models. However, these features may correlate to other clinical features from the model spaces and may be only implicitly relevant to evaluate the mechanistic model parameters. These are referred to herein as implicitly relevant features, or simply "implicit features." The generative model in one or more illustrative embodiments may be modified to take in account such type of implicitly relevant features (see FIG. 3 described hereafter). Here, distribution of a clinical feature set is replaced by a conditional distribution with respect to implicitly relevant features which are also fed to the ML model.

To illustrate the benefits of the mechanisms of the illustrative embodiments, consider an example of training a generative model to match the changes in the clinical feature set measured in patients upon administration of cardiac inotropes, i.e. drugs that change the strength of the heart contraction. The clinical features, such as duration of cardiac contraction, stroke volume, etc. measured from echocardiography are observed in the population of patients before and after administration of the cardiac inotropes. Training of the generative model represents the mapping of a distribution of these clinically observed features (reproducible by the mechanistic models) to the parameter space of the mechanistic models, producing a generative model as a result of training. Mapping of observable data to the parameter space of the mechanistic model allows improved interpretation of the mechanism of the action of the drug and extraction of novel biomarkers. The "prior" information (constraints) for this particular example can be simply the bounds (ranges) of mechanistic model parameters such as parameters regulating the calcium ion transient in the cells (that may be estimated from cellular experiments in different species). The trained generative model can be used to estimate a distribution of the mechanistic model parameters to match the distribution of features in the absence of the drug and also the distribution of features in the presence of the drug. The differences in the estimated distributions of mechanistic model parameters provide an indication of the mechanism of the action of the drug.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

Furthermore, the present description makes reference to machine learning and machine learning processes to train machine learning computer models. It should be appreciated that the machine learning may be performed using any known or later developed machine learning algorithms. For example, machine learning algorithms that may be used to train one or more of the various machine learning models of the illustrative embodiments may include decision tree, random forest, support vector machines, K nearest neighbors, linear regression, or the like.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As mentioned above, the illustrative embodiments provide an improved computer tool and computer tool methodology that implements a hybrid computer model mechanism for inferring, constructing, and presenting personalized illustrative biophysical models from explicitly and implicitly relevant clinical feature sets. The illustrative embodiments combine mechanistic models of biological systems with machine learning models that are specifically trained to predict pathophysiological states of patients based on high level patient data from patient electronic medical records. The combined mechanistic models and machine learning models together constitute a hybrid computer model in accordance with the illustrative embodiments.

The mechanisms of the illustrative embodiments provide a mechanistic model, or in some illustrative embodiments referred to as a biophysical model, which is configured to transform model parameters into simulated data of a modeled biological system, e.g., patient data inputs for defining a biological system particular to a patient, such as heart geometry data for a cardiac mechanistic model, into predicted patient features such as an electrocardiogram (ECG) signal data, electroencephalogram (EEG) signal data, medical imaging data, pressure-volume trace, etc. that are influenced by the input model parameters through the functions defining the mechanistic model. The mechanistic model may be any known or later developed mechanistic model that models the operation of a real-world system, such as a patient's biological system, e.g., cardiac system, pulmonary system, nervous system, endocrine system, immune system, lymphatic system, etc.

The mechanistic model creates a training dataset which is then used to train a surrogate machine learning model. The surrogate machine learning model is trained to be a proxy for the mechanistic model since the machine learning model is able to infer outputs based on inputs and the operational parameters learned through machine learning. The mechanistic model generates outputs based on particular inputs, which are considered a ground truth for the inputs, whether or not the outputs are in fact true or not. That is, the purpose of training the surrogate machine learning model is to have the surrogate machine learning model replicate the operation of the mechanistic model, whether that mechanistic model is accurate or not, and thus the surrogate machine learning model is trained to output the same outputs as the mechanistic model given the same inputs, as specified in the training data generated by the mechanistic model.

Thus, the pairing of inputs and outputs generated by the mechanistic model are used as a training dataset for the surrogate machine learning (ML) model. The surrogate ML model is able to rapidly interpolate model states that would otherwise require dense sampling of a parameter space using the mechanistic model. The surrogate ML model is differentiable through backpropagation and is therefore available for subsequent transfer learning that employs the surrogate ML model in the training task.

Thus, the surrogate ML model takes as input model parameters of non-invasively measurable patient data, such as the heart geometry of a patient, and generates predicted patient features, such as patient signal data (ECG, EEG, etc.), for example. The training of the surrogate ML model causes the surrogate ML model to learn relationships between the input patient data, or mechanistic model parameters, and hidden patient pathophysiological states that are not able to be measured non-invasively and which are represented by hidden layers of the surrogate ML model. For example, the surrogate ML model may be trained to learn the relationship between a cardiac mechanistic model's input parameters and its measure of ventricular contraction efficiency. The hidden patient pathophysiological states are characterized by indices and biomarkers that are calculated as functions of mechanistic model parameters obtained after training of the generative model. Some clinically useful indices may be generated by additional protocols using the mechanistic model and the parameters inferred from the training. For instance, different protocols of heart contraction may be simulated to obtain an end-systolic pressure volume relationship that characterizes contractility of the heart.

The illustrative embodiments further provide a transformation ML model that is trained through a machine learning process to receive patient feature data, such as that predicted by the surrogate ML model, and transform or predict patient outcomes or categories based on the received patient feature data. During training of the transformation ML model, ground truth outcomes or categories may be derived from labels or associated with labels in a patient medical record, e.g., medical conditions of a patient or categories of medical conditions of a patient. That is, for a particular patient, patient feature data may be recorded, such as ECG data, EEG data, etc. and a corresponding label or category of medical condition, such as a prognosis label, may be associated with the patient, e.g., a prognosis label of "transcatheter aortic valve replacement (TAVR), failure observed 6 months later." The patient feature data generated by the surrogate ML model may be input to the transformation ML model which generates an output classification of a predicted prognosis label that may be compared to the prognosis label associated with the recorded patient feature data. A loss is calculated based on this comparison which can then be used to train the transformation ML model using a machine learning process to adjust the operational parameters, e.g., weights, of the transformation ML model. This process may be repeated for each portion of training data used to train the transformation ML model.

Thus, for example, input patient data (or model parameters) $X1$, $X2$, ... $Xn$, such as heart geometry data, for example, may be input to the surrogate ML model which models the mechanistic biological system of interest, such as a cardiac system, with a machine learning model, and generates patient features $F1$, $F2$, ... $Fm$, such as an EEG signal, ECG signal, or the like. These generated patient features may then be input to the trained transformation ML model which predicts outcomes or categories of patient medical conditions based on its training. In some illustrative embodiments, the transformation ML model learns a distribution of latent (hidden) variables, i.e. variables that are not observed from the real world but may be indirectly inferred from observations, coherent to a distribution of observed data, e.g., distribution of the patient features $F1$, $F2$, ... $Fm$, such as features in the ECG or EEG signal, pressure-volume traces, etc. In the illustrative embodiments, the latent variables are mechanistic model parameters.

In addition to training a surrogate ML model and a transformation ML model, the mechanisms of the illustrative embodiments further train a generative ML model to generate samples of input data that are input to the biophysical model, i.e. the surrogate ML model, by sampling from a uniform distribution using a pseudo-random number generator, for example. The "generative model" is a model of the conditional probability of the observable variable X, given a target variable Y. An encoder of the generative model encodes samples of the uniform distribution as samples of the mechanistic model parameters from the distribution that are coherent with an observable feature set. The encoder is trained, through the mechanisms of the illustrative embodiments using transfer learning based on the loss calculated for downstream ML models (where "downstream" refers to components that later in a data flow direction than other components), such as the transformation ML model and a "prior" ML model, as described hereafter, to generate samples of patient data or model parameters that are input to the surrogate ML model, from the uniform distribution where these samples are consistent with real patient data distributions. The samples X1, X2, ..., Xn generated by the encoder are input model parameters, e.g., input patient data, to the surrogate ML model, which then operates on these inputs as discussed previously to generate patient feature data which is then provided as input to the transformation ML model which generates predicted output classifications/distributions. The term "prior" as it is used herein refers to the concept in Bayesian statistical inference of a prior probability distribution of an uncertain quantity being the probability distribution that would express one's beliefs about this quantity before evidence is taken into account. In the context of the present invention, these "priors" represent given or learned constraints on parameters or data of one or more of the machine learning models.

During training of the generative model, and specifically the encoder of the generative model, the output of the transformation ML model may be used to calculate a loss. In one illustrative embodiment, the loss is formulated as a test for uniformity of the output of the transformation ML model generated by feeding a mini-batch of samples of the uniform distribution to the encoder, which propagates through the graph of the model to the output. The uniformity of the output is enforced by maximizing mutual information between inputs and outputs using, for example, an infomax algorithm or quantifying and minimizing clustering in the output data generated by a single mini-batch. The loss may be backpropagated to the encoder to adjust its operational parameters which define the transformation in the encoder so as to modify the encoder's sample generation.

The illustrative embodiments further comprise a "prior" model that is trained to ensure that any requirements or constrains on the sampled model parameters, or input patient data to the surrogate ML model, are followed by the encoder when sampling from the uniform distribution input. The "prior" model is represented by a transformation from the given "prior" distribution to the uniform distribution, and the "prior" information is incorporated in the training process by enforcing uniformity of the output, such as by infomax or checking for clustering in output data, for example. The losses generated by the "prior" model and the transformation ML model may be backpropagated to the generative model to train the sampling logic of the encoder of the generative model.

Thus, having trained the surrogate ML model, the transformation ML model, the "prior" model, and the generative model comprising the encoder, these trained models are combined into a hybrid model that combines the mechanistic model structure represented in the surrogate ML model due to its training based on training data used to train the surrogate ML model as generated by a mechanistic model, with the machine learning features of the transformation ML model. Moreover, the encoder of the generative model is specifically trained to ensure that the samples it generates for input to the surrogate ML model are consistent with the distribution of samples seen in real world datasets, e.g., distributions of patient data. Furthermore, the "prior" model ensures that these samples comply with established constraints or requirements.

FIG. 1 is an example diagram of a hybrid model in accordance with one illustrative embodiment. It should be appreciated that in FIG. 1, each of the models, which are computer machine learning models, are executed on one or more processors of one or more computing devices. These may all be provided in the same specifically configured computing device or may be distributed across multiple different computing devices, each of which is specifically configured to implement the particular models attributed to them. The individual models 110, 120, 130, and 140 are specifically trained in the manner previously described above using machine learning processes, such as stochastic gradient descent, alternating minimization, or the like, based on loss determinations using a loss function, or any other suitable known or later developed machine learning process.

As shown in FIG. 1, the hybrid model 100 is again a computer model that requires execution of the logic of the hybrid model 100 within one or more computing devices of a data processing system, where these one or more computing devices then become specially configured computing devices that are specifically configured to implement the elements of the hybrid model 100. The hybrid model 100 includes a generative model 110 comprising an encoder 114 that receives samples from a uniform distribution U1, U2, ... Un, and generates samples of model parameters, e.g., input patient data such as the geometry of a heart or the like, X1, X2, . . . Xn 116. The samples from the uniform distribution 112 may be generated by using a pseudo-random number generator, for example, to select samples from the uniform distribution. The general patient data is potentially weakly-related to the biophysical functions of the biological system that is modeled using a mechanistic model, or modeled by the proxy surrogate ML model 120. The encoder 114 is trained to generate model parameters, e.g., patient data inputs to the surrogate ML model 120, from the random numbers with the uniform distribution 112 using a pseudo-random number generator, for example.

During training of the encoder 114 of the generative model 110, the samples of model parameters 116 output by the encoder 114 are input to both a surrogate ML model 120 and a "prior" model 140. It should be noted that after training, the "prior" model 140 will not be utilized during the runtime operation of the trained encoder 114.

The "prior" model 140, as discussed above, operates on the samples of model parameters 116 to ensure that the samples comply with given or learned constraints and requirements. The prior model 140 may be trained to learn whether input samples meet with constraints and requirements again through a machine learning process (e.g., decision tree, random forest, support vector machines, K nearest neighbors, linear regression, or the like) and as such may generate a loss output 142. This loss output 142 may initially be used to train the prior model 140 based on training data and ground truth. However, after training the prior model 140 itself, the prior model 140 may be applied to the samples of model parameters 116 generated by the encoder 114 during training of the encoder 114 and the generated loss 142 may be backpropagated to the encoder 114 to modify its operational parameters, e.g., weights and the like, so as to minimize this loss and cause the encoder 114 to select samples of model parameters 116 that meet with the constraints and requirements enforced by the prior model 140.

The samples of model parameters 116 are also input to the surrogate ML model 120 which is a machine learning trained computer model that is trained using a mechanistic model generated training dataset and approximates the operation of the mechanistic model. The surrogate ML model 120 processes the model parameters X1, X2, . . . Xn 116, e.g., patient data such as the geometry of a human heart, and predicts feature data outputs F1, F2, . . . , Fm 122, such as ECG signal data, EEG signal data, or the like. The predicted patient feature data 122 is input to a trained transformation ML model 130. The trained transformation ML model 130 provides an encoding of the feature distribution of the predicted patient feature data 122 generated by the surrogate ML model 120 in the form of a transformation from samples of the feature distribution to samples of a uniform distribution. Any other distribution than the feature distribution of the patient feature data passed through the transformation of the transformation ML model 130 would produce a non-uniform distribution, and its deviation from uniform may be used as a loss function to train a better sampling of the distribution by the encoder 114.

The trained transformation ML model 130 is trained based on a training dataset comprising patient feature data inputs and correct classification label outputs, using a machine learning process such as stochastic gradient descent, alternating minimization, or the like. The transformation ML model 130 outputs classification labels for a patient based on the predicted features 122 generated by the surrogate ML model 120, which generates these predicted features 122 based on samples of patient data (model parameters) 116 encoded by the encoder 114 from a uniform distribution 112. Thus, given a uniform distribution 112 generated by a pseudo-random number generator, for example, the hybrid model 100 is trained to output a classification label output by the transformation ML model 130 that takes into account the influence of hidden patient pathophysiological states represented by hidden layers of the surrogate ML model 120.

During training of the encoder 114, the loss 132 of the output of the transformation ML model 130 may be back-propagated to the encoder 114 to thereby modify the operational parameters of the encoder 114, e.g., weights in the case of the encoder being implemented as a machine learning model. Thus, the loss 132 from the transformation ML model and the loss 142 from the prior model 140 may both be back propagated to the generative model 110 to thereby train the encoder 114 through a machine learning process using machine learning logic, to modify the operational parameters of the encoder 114 to select samples of model parameters, e.g., patient data, 116 that both satisfy known constraints or requirements (as enforced by the loss 142 from the prior model 140) and are consistent with real-world distributions of model parameters such as patient data (as enforced by the loss 132 from the transformation ML model 130). The loss functions 132 and 142 enforce distributions to be normal or uniform at the output of the ML models 130 and 140.

The result of this architecture is that the hybrid model 100 combines the advantages of statistical models represented as machine learning computer models, with mechanistic models by providing a particular arrangement of trained machine learning computer models and a particular training methodology involving transfer learning where the loss of one or more machine learning models, e.g., the transformation ML model and the prior model, is used to adjust the operational parameters of another machine learning model, e.g., the encoder. The trained models are combined in a particular way such that the encoder is able to convert a uniform distribution into input model parameters of a surrogate ML model, which then generates features for input to the transformation ML model, which generates classification outputs based on the input features. Mechanistic models provide only hypotheses for further testing and operate on a small set of available data. Statistical models provide predictions that are difficult to interpret. A hybrid model approach, in accordance with the illustrative embodiments, which combines the mechanistic models and statistical models provides a solution that can assess the distribution of deterministic model parameters to estimate mechanistic causes for predictions generated by the statistical models. Thus, for example, a hybrid model 100 may estimate mechanistic causes of preclinical and clinical data and incorporate prior mechanistic knowledge into models of clinical outcomes.

The approach described herein with regard to the illustrative embodiments provides several benefits as compared with regular statistical methods. First, important hidden variables may be evaluated where registration of such hidden variables would otherwise require complex experimental setups for in-vitro tests or invasive clinical measurements for patient diagnostics. Second, the data from experiments or clinical tests with different settings can be melded in the parameter space of the illustrative embodiments. Finally, the approach of the illustrative embodiments presents a clear way to incorporate prior knowledge about a biological system to the statistical model of the illustrative embodiments to improve statistical model predictions. Possible applications of the approach of the illustrative embodiments may include, for example, the cardiac inotropes example previously mentioned above, as well as a plethora of other medical and non-medical domain applications.

Figure 2A:
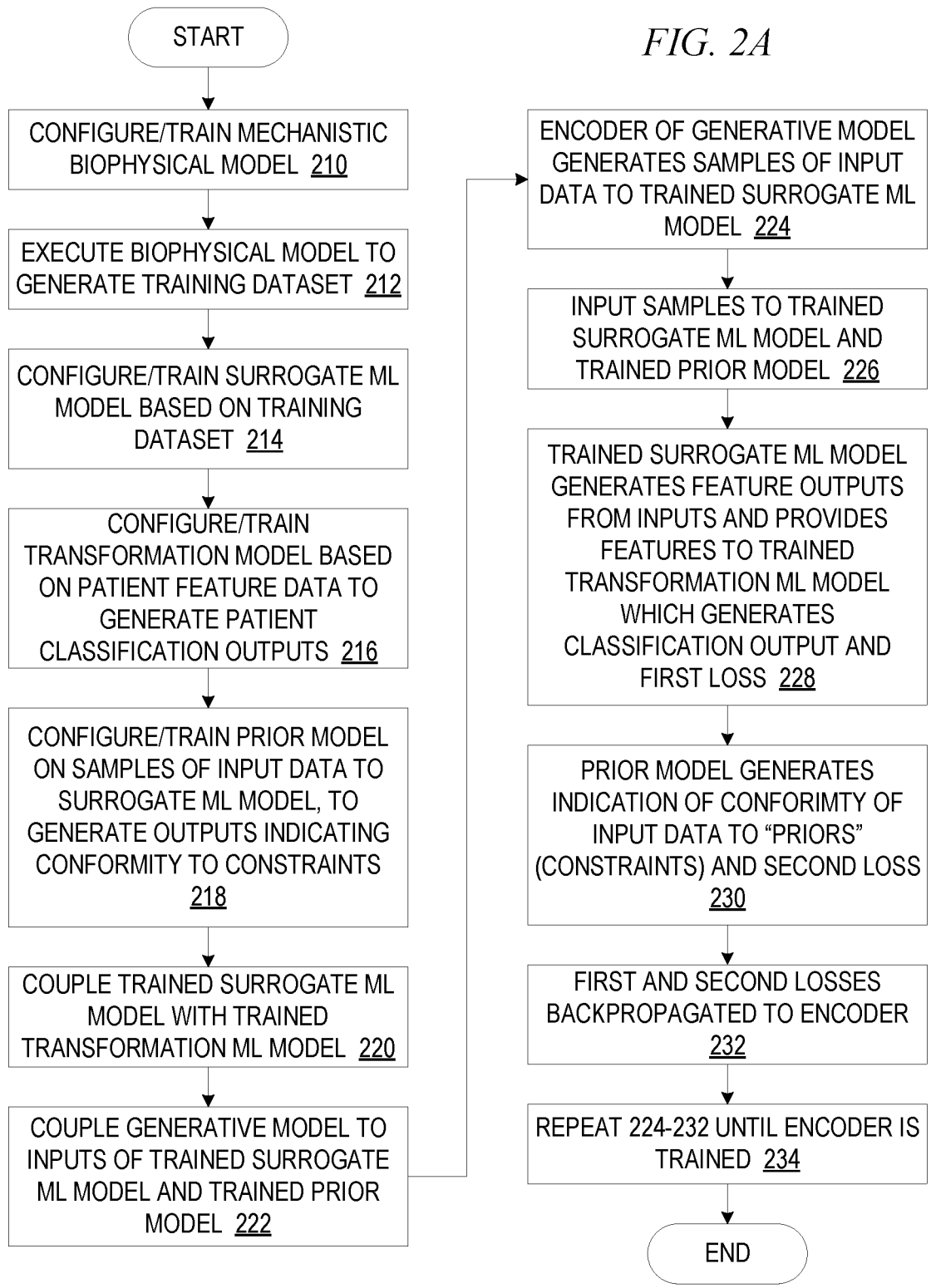
FIG. 2A is a flowchart outlining an example operation for training a hybrid model in accordance with one illustrative embodiment.

FIG. 2A is a flowchart outlining an example operation for training a hybrid model in accordance with one illustrative embodiment. The operation outlined in FIG. 2A assumes that the hybrid model is being used to model biophysical properties of a human patient, however as noted above, the present invention is not limited to such and can be used to model any system in which subsystems may be represented as mechanistic processes in mechanistic models.

As shown in FIG. 2A, the operation starts by configuring and training a mechanistic biophysical model to model a biological system of a patient (step 210). The mechanistic biophysical model is executed multiple times on input data representing patient data to generate patient feature outputs, where the combination of input patient data and output patient features together constitute a training dataset for training a surrogate ML model (step 212). A surrogate ML model is then configured and trained based on the training dataset generated by the mechanistic model (step 214). A transformation ML model is trained based on patient feature data to generate patient classification outputs (step 216). A prior model is configured and trained on samples of input data to the surrogate ML model to generate outputs indicating conformity of the samples of input data to constraints or requirements of the sampled input data (step 218).

The trained surrogate ML model is coupled with the trained transformation ML model such that the output of the trained surrogate ML model is provided as input to the trained transformation ML model (step 220). A generative model, comprising a machine learning based encoder, is coupled to the inputs of the trained surrogate ML model and the trained prior model (step 222). The encoder generates samples of input data to the trained surrogate ML model based on an input uniform distribution (step 224). These samples are input to the trained surrogate ML model and the trained prior model (step 226). The trained surrogate ML model generates feature outputs from the inputs received from the encoder and provides those features to the trained transformation ML model which generates a classification output and a first loss (step 228). The prior model generates an indication of whether or not the input data generated by the encoder conforms with "priors" or constraints and also generates a second loss (step 230). The first and second losses are backpropagated to the encoder to thereby modify the operational parameters of the encoder (step 232). This operation, e.g., steps 224-232, continues until training of the encoder converges and the first and second losses are minimized to a predetermined threshold (step 234). The operation then terminates.

Figure 2B:
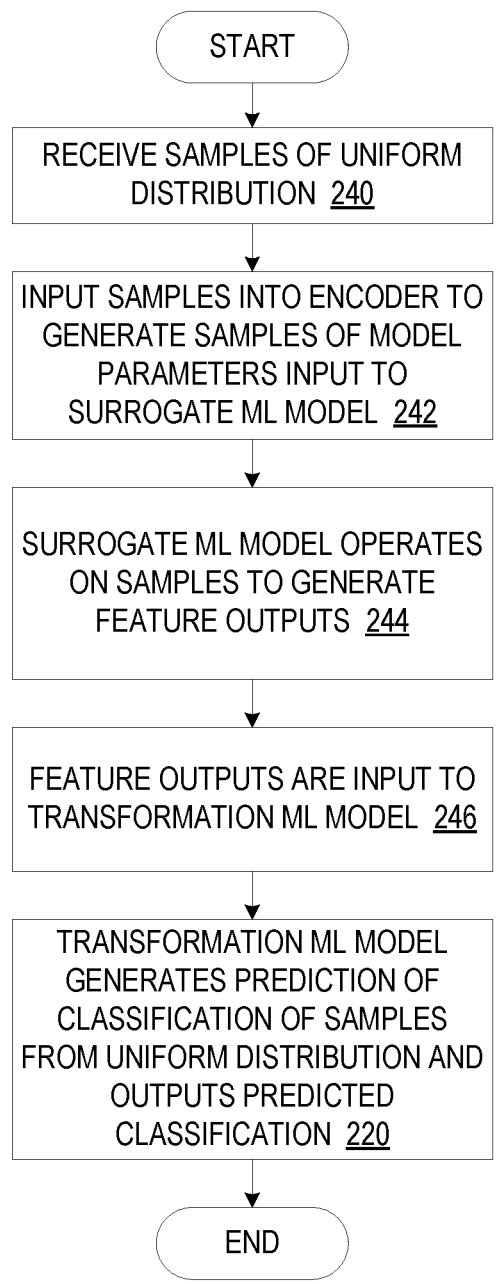
FIG. 2B is a flowchart outlining an example operation of processing patient data to generate a predicted classification based on hidden patient pathophysiological states in accordance with one illustrative embodiment.

FIG. 2B is a flowchart outlining an example operation of processing patient data to generate a predicted classification based on hidden patient pathophysiological states in accordance with one illustrative embodiment. As shown in FIG. 2B, the operation starts by receiving samples of random variable with a uniform distribution generated by pseudo-random number generator, for example (step 240). The received samples are input to an encoder of the generative model which generates samples of model parameters, i.e. input data to a surrogate ML model, (step 242). The surrogate ML model operates on the samples of model parameters to generate feature outputs (step 244). The feature outputs are input to a transformation ML model (step 246) and the transformation ML model generates a prediction of a classification of the samples from the uniform distribution that is output (step 248). The operation then terminates.

Using the mechanisms of the illustrative embodiments, clinicians are able to use biomarkers and clinical indices calculated from parameters of the mechanistic model for additional interpretation of statistical model predictions. Moreover, hidden pathophysiological metrics may be identified and used for classification of patient state based on statistics derived from the distribution of mechanistic model parameters obtained by the generative model of the illustrative embodiments.

These biomarkers and clinical indices may be output with the output of predictions of the classifications of the samples from the uniform distribution as further evidence in support of the classification or reasoning information, such as in a graphical user interface, or other visualization of the classification output. Thus, for example, in the case of a cardiac mechanistic model being employed, the surrogate ML model may identify hidden pathophysiological features of a patient, such as the intraventricular pressure, myocardial strains, etc. whose values may be output along with a patient classification of "transcatheter aortic valve replacement (TAVR), failure observed 6 months later", to thereby give the clinician more information for understanding or interpreting the prediction and the root causes of the prediction, especially with regard to pathophysiological features that are difficult to measure apart from invasive instrumentation or that are currently impossible to measure.

Figure 3:
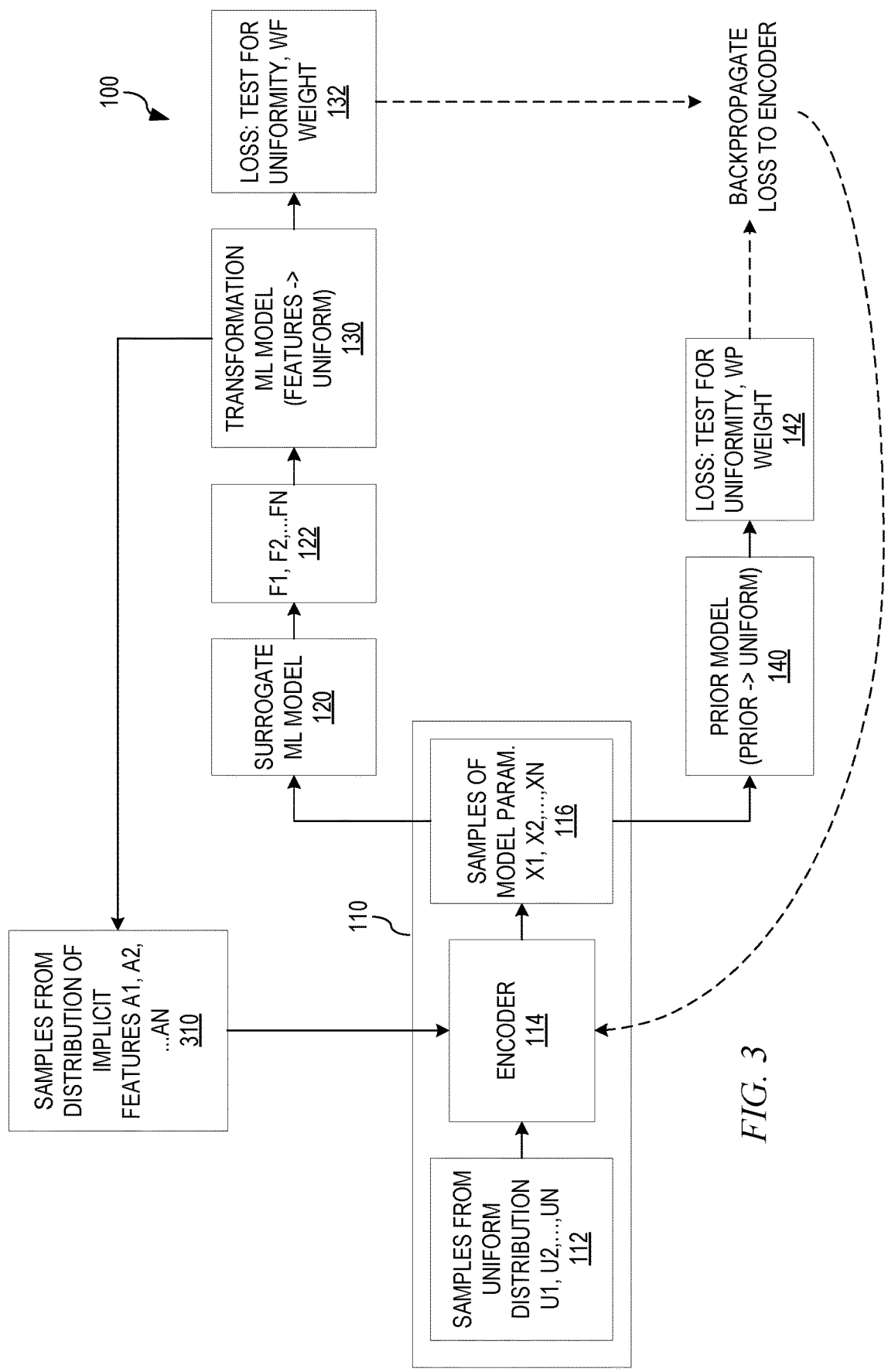
FIG. 3 is an example block diagram of a hybrid model architecture that accounts for the implicitly relevant data in accordance with one illustrative embodiment.

FIG. 3 is an example block diagram of a hybrid model architecture that accounts for the implicitly relevant data in accordance with one illustrative embodiment. As shown in FIG. 3, the alternative hybrid model architecture of FIG. 3 is similar to the architecture shown in FIG. 1 and described above, with the exception that the encoder 114 also receive implicit features A1, A2, ... An 310 from the transformation ML model 130 as input for training this machine learning model 114 to sample from the uniform distribution 112 and generate samples of mechanistic model parameters. As discussed previously, the hybrid model 100 includes a generative model 110 comprising an encoder 114 that receives samples from a uniform distribution U1, U2, ... Un, and generates samples of mechanistic model parameters, e.g., input patient data such as the geometry of a heart or the like, X1, X2, ... , Xn 116 that are input to the surrogate ML model 120. In this alternative embodiment, the encoder 114 also takes as input a set of implicitly relevant patient data that cannot be reproduced from the output of the mechanistic model or surrogate ML model 120, and does not belong to the input of the surrogate ML model 120. Examples of such implicitly relevant patient data include temperature, age, gender, race, etc.

For example, the implicitly relevant features may be the set of experimental/clinical features that are neither the input or outputs of the mechanistic model but can have an impact on the predictions generated by the statistical machine learning model. For example, a patient's age is typically not accounted for by the mechanistic models. However, in some illustrative embodiments of the present invention, such implicitly relevant patient data may be considered in estimation of the mechanistic model parameters that match the clinical features (reproduced by the mechanistic model). As another example of implicitly relevant features, the temperature at which an in vitro experiment is carried out to characterize the effects of cardiac drugs may be provided. The temperature and conditions differ across different experimental setups and can have impact on the measured features. For example, the rates of cellular processes that are used as inputs to the mechanistic model vary with temperature and can have significant effects on the predictions, however, the mechanistic models do not account for the temperature-based changes. In the hybrid model of at least some of the illustrative embodiments, these implicit features are added as additional inputs to the encoder 114 as additional training input data upon which the encoder 114 is trained using the machine learning process previously discussed above.

Figure 4:
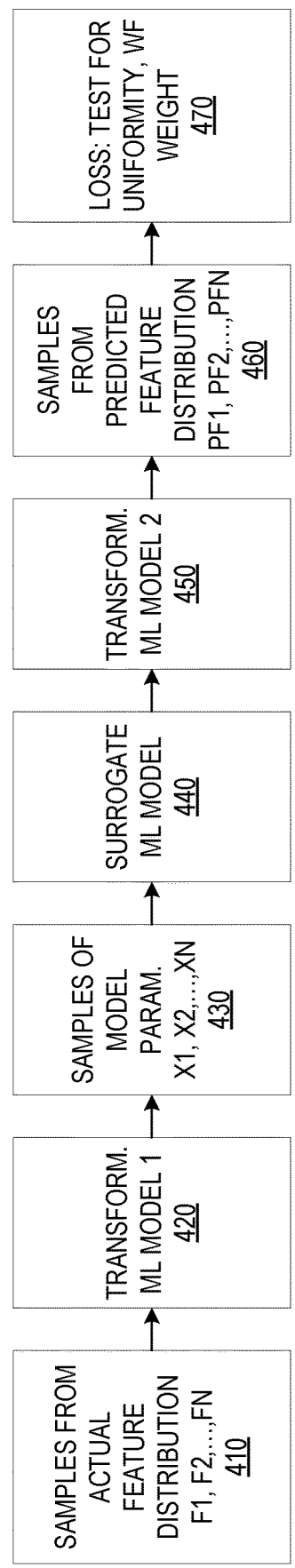
FIG. 4 is example block diagram of alternative hybrid model architecture in the case of invertible mechanistic models in accordance with one illustrative embodiment.

FIG. 4 is example block diagram of alternative hybrid model architecture in the case of invertible mechanistic models in accordance with one illustrative embodiment. In this example, the generative model is trained as part of an identify transformation for a feature set 410 obtained from physical observations. The identity transformation is represented as a chain of transformations from the observed features to mechanistic model parameters, from mechanistic model parameters to mechanistic model outputs, and from the mechanistic model outputs to the observed features.

As shown in FIG. 4, in the case of an invertible mechanistic model a simpler hybrid model architecture is provided that is comprised of machine learning models that perform the chain of transformation noted above. That is, the simpler hybrid model architecture includes a first transformation ML model 420 that receives samples 410 from a distribution of clinical data measures (F1, F2, . . . Fm) and generates samples of mechanistic model parameters 430, e.g., input patient data such as the geometry of heart X1, X2, . . . Xn. The first transformation ML model 420 operates similar to the encoder 114 in FIG. 1, but takes as inputs the samples from the distribution of clinical data measures, i.e. observed features. Since the mechanistic model is invertible, a transformation may be built from the clinical data measures to the mechanistic model parameters, which is otherwise not possible for non-invertible mechanistic models as multiple parameter sets can give the same output features (this is why there is an encoder 114 in the illustrative embodiment of FIG. 1 that transforms the random variable U1, U2, . . . Un with normal or uniform distribution to the distribution of mechanistic model parameters). The surrogate ML model 440 receives these mechanistic model parameters 430 and generates outputs to a second transformation ML model 450 that predicts samples of a predicted feature distribution, e.g., clinical data (PF1, PF2, . . . PFn).

In the case of this simpler invertible mechanistic model embodiment, the architecture may be trained using data features (F1, F2, . . . Fm) that are not directly reproduced by the mechanistic model but are related to the mechanistic model output by the transformation. The second transformation ML model 450 is an additional ML model layer that transforms the features generated by the surrogate ML model to reproduce the observed features F1, F2, . . . Fm as the samples from the predicted feature distribution 460.

Figure 5:
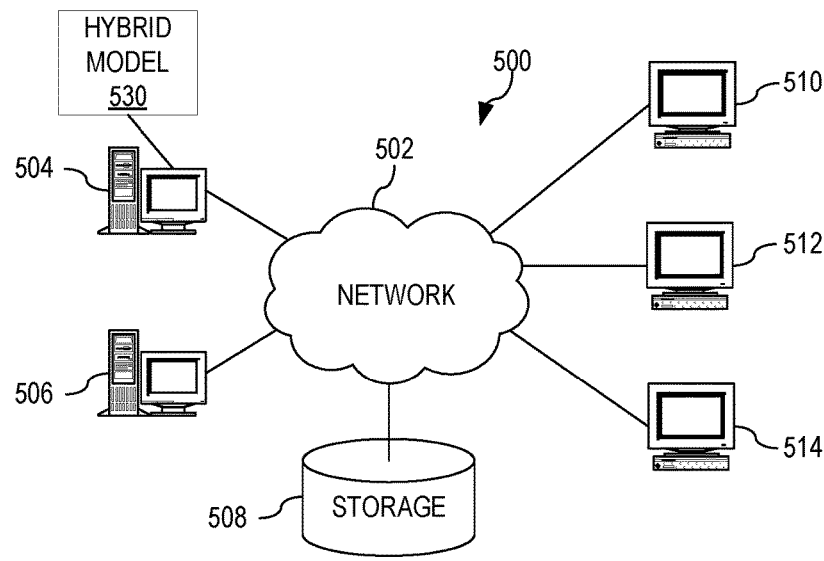
FIG. 5 is an example diagram of a distributed data processing system in which aspects of the illustrative embodiments may be implemented.
Figure 6:
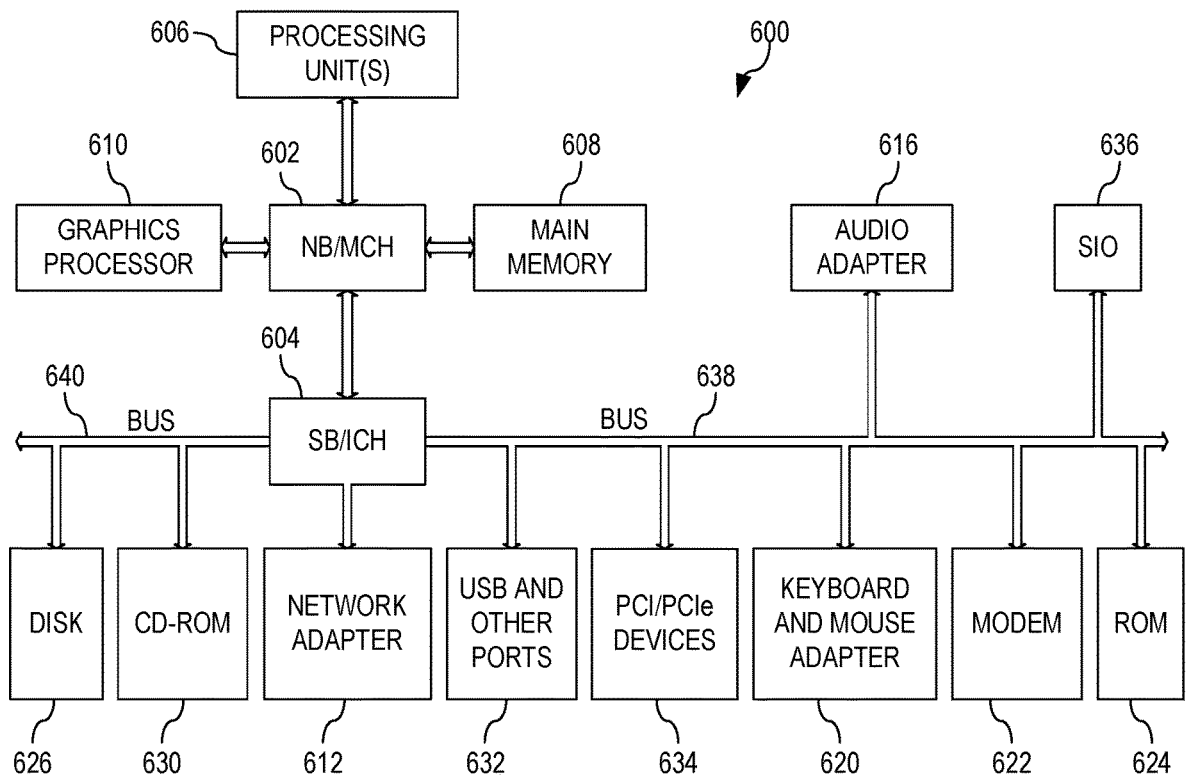
FIG. 6 is an example block diagram of a computing device in which aspects of the illustrative embodiments may be implemented.

From the above discussion, it is apparent that the present invention is specifically directed to an improved computer tool and specific computer tool methodology for assisting clinicians in the identification of pathophysiological features indicative of disease and adverse medical conditions. As an improved computer tool and computer tool methodology, the illustrative embodiments may be utilized in many different types of data processing environments. In order to provide a context for the description of the specific elements and functionality of the illustrative embodiments, FIGS. 5 and 6 are provided hereafter as example environments in which aspects of the illustrative embodiments may be implemented. It should be appreciated that FIGS. 5 and 6 are only examples and are not intended to assert or imply any limitation with regard to the environments in which aspects or embodiments of the present invention may be implemented. Many modifications to the depicted environments may be made without departing from the spirit and scope of the present invention.

FIG. 5 depicts a pictorial representation of an example distributed data processing system in which aspects of the illustrative embodiments may be implemented. Distributed data processing system 500 may include a network of computers in which aspects of the illustrative embodiments may be implemented. The distributed data processing system 500 contains at least one network 502, which is the medium used to provide communication links between various devices and computers connected together within distributed data processing system 500. The network 502 may include connections, such as wire, wireless communication links, or fiber optic cables.

In the depicted example, server 504 and server 506 are connected to network 502 along with storage unit 508. In addition, clients 510, 512, and 514 are also connected to network 502. These clients 510, 512, and 514 may be, for example, personal computers, network computers, or the like. In the depicted example, server 504 provides data, such as boot files, operating system images, and applications to the clients 510, 512, and 514. Clients 510, 512, and 514 are clients to server 504 in the depicted example. Distributed data processing system 500 may include additional servers, clients, and other devices not shown.

In the depicted example, distributed data processing system 500 is the Internet with network 502 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 500 may also be implemented to include a number of different types of networks, such as for example, an intranet, a local area network (LAN), a wide area network (WAN), or the like. As stated above, FIG. 5 is intended as an example, not as an architectural limitation for different embodiments of the present invention, and therefore, the particular elements shown in FIG. 5 should not be considered limiting with regard to the environments in which the illustrative embodiments of the present invention may be implemented.

As shown in FIG. 5, one or more of the computing devices, e.g., server 504, may be specifically configured to implement a hybrid computer model 530. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 504, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, in some illustrative embodiments, the implementation of the mechanisms of the illustrative embodiments improves the functionality of the computing device and provides a useful and concrete result that facilitates generating biomarkers and clinical indices calculated from parameters of the mechanistic model for additional interpretation of statistical model predictions by a clinician, melding results of experiments with different settings in the parameter space of mechanistic model, and evaluating hidden characteristics of biological systems based on a hybrid computer model generated and trained in the manner previously described above.

As noted above, the mechanisms of the illustrative embodiments utilize specifically configured computing devices, or data processing systems, to perform the operations for training a hybrid computer model that combines the mechanistic model and statistical model features discussed above to provide insights regarding hidden pathophysiological features influencing patient classifications and outcomes in accordance with the illustrative embodiments as described previously. These computing devices, or data processing systems, may comprise various hardware elements which are specifically configured, either through hardware configuration, software configuration, or a combination of hardware and software configuration, to implement one or more of the systems/subsystems described herein. FIG. 6 is a block diagram of just one example data processing system in which aspects of the illustrative embodiments may be implemented. Data processing system 600 is an example of a computer, such as server 504 in FIG. 5, in which computer usable code or instructions implementing the processes and aspects of the illustrative embodiments of the present invention may be located and/or executed so as to achieve the operation, output, and external effects of the illustrative embodiments as described herein.

In the depicted example, data processing system 600 employs a hub architecture including north bridge and memory controller hub (NB/MCH) 602 and south bridge and input/output (I/O) controller hub (SB/ICH) 604. Processing unit 606, main memory 608, and graphics processor 610 are connected to NB/MCH 602. Graphics processor 610 may be connected to NB/MCH 602 through an accelerated graphics port (AGP).

In the depicted example, local area network (LAN) adapter 612 connects to SB/ICH 604. Audio adapter 616, keyboard and mouse adapter 620, modem 622, read only memory (ROM) 624, hard disk drive (HDD) 626, CD-ROM drive 630, universal serial bus (USB) ports and other communication ports 632, and PCI/PCIe devices 634 connect to SB/ICH 604 through bus 638 and bus 640. PCI/PCIe devices may include, for example, Ethernet adapters, add-in cards, and PC cards for notebook computers. PCI uses a card bus controller, while PCIe does not. ROM 624 may be, for example, a flash basic input/output system (BIOS).

HDD 626 and CD-ROM drive 630 connect to SB/ICH 604 through bus 640. HDD 626 and CD-ROM drive 630 may use, for example, an integrated drive electronics (IDE) or serial advanced technology attachment (SATA) interface. Super I/O (SIO) device 636 may be connected to SB/ICH 604.

An operating system runs on processing unit 606. The operating system coordinates and provides control of various components within the data processing system 600 in FIG. 6. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 600.

As a server, data processing system 600 may be, for example, an IBM eServer™ System p® computer system, Power™ processor based computer system, or the like, running the Advanced Interactive Executive (AIX®) operating system or the LINUX® operating system. Data processing system 600 may be a symmetric multiprocessor (SMP) system including a plurality of processors in processing unit 606. Alternatively, a single processor system may be employed.

Instructions for the operating system, the object-oriented programming system, and applications or programs are located on storage devices, such as HDD 626, and may be loaded into main memory 608 for execution by processing unit 606. The processes for illustrative embodiments of the present invention may be performed by processing unit 606 using computer usable program code, which may be located in a memory such as, for example, main memory 608, ROM 624, or in one or more peripheral devices 626 and 630, for example.

A bus system, such as bus 638 or bus 640 as shown in FIG. 6, may be comprised of one or more buses. Of course, the bus system may be implemented using any type of communication fabric or architecture that provides for a transfer of data between different components or devices attached to the fabric or architecture. A communication unit, such as modem 622 or network adapter 612 of FIG. 6, may include one or more devices used to transmit and receive data. A memory may be, for example, main memory 608, ROM 624, or a cache such as found in NB/MCH 602 in FIG. 6.

As mentioned above, in some illustrative embodiments the mechanisms of the illustrative embodiments may be implemented as application specific hardware, firmware, or the like, application software stored in a storage device, such as HDD 626 and loaded into memory, such as main memory 608, for executed by one or more hardware processors, such as processing unit 606, or the like. As such, the computing device shown in FIG. 6 becomes specifically configured to implement the mechanisms of the illustrative embodiments and specifically configured to perform the operations and generate the outputs described herein with regard to the hybrid computer model.

Those of ordinary skill in the art will appreciate that the hardware in FIGS. 5 and 6 may vary depending on the implementation. Other internal hardware or peripheral devices, such as flash memory, equivalent non-volatile memory, or optical disk drives and the like, may be used in addition to or in place of the hardware depicted in FIGS. 5 and 6. Also, the processes of the illustrative embodiments may be applied to a multiprocessor data processing system, other than the SMP system mentioned previously, without departing from the spirit and scope of the present invention.

Moreover, the data processing system 600 may take the form of any of a number of different data processing systems including client computing devices, server computing devices, a tablet computer, laptop computer, telephone or other communication device, a personal digital assistant (PDA), or the like. In some illustrative examples, data processing system 600 may be a portable computing device that is configured with flash memory to provide non-volatile memory for storing operating system files and/or user-generated data, for example. Essentially, data processing system 600 may be any known or later developed data processing system without architectural limitation.

Thus, the illustrative embodiments provide mechanisms for implementing a hybrid computer model that combines the prior knowledge of biological systems as represented in mechanistic models with statistical analysis represented in machine learning models to generate a hybrid solution that provides mechanistic reasoning for statistically generated patient classifications. The illustrative embodiments first use a mechanistic model to generate training data to train a surrogate machine learning model that models the biophysical behavior of a biological system. The illustrative embodiments further train a transformation machine learning model to predict patient categories or classifications based on patient feature data generated by the surrogate machine learning model. The illustrative embodiments further train a "prior" machine learning model or constraint model that ensures that samples of input data to the surrogate machine learning model are constrained to known (prior) constraints of the input data. Furthermore, an encoder is trained based on the operations of the trained surrogate machine learning model, the trained transformation machine learning model, and the trained prior model, to generate samples of input data to the surrogate machine learning model that match observable distributions of real-world data.

In some illustrative embodiments, mechanisms, in an apparatus, system, method, and/or computer program product, are provided that are capable of predicting parameters of a biophysical model of patient pathophysiology from input medical data. These mechanisms include a primary mechanistic model, which associates patient data with other patient data, data features, and data labels, where the type of the patient primary data is commensurate with the outputs of a biophysical model, and the labels comprising medical features, reports, outcomes, diagnoses, prognoses, or progression states. The mechanisms further include a secondary machine learning model, e.g., the surrogate machine learning model, trained to predict biophysical model outputs from biophysical model parameters, the outputs comprising data commensurate with patient data. The mechanisms also include a tertiary machine learning model, e.g., the transformation machine learning model, capable of transforming input candidate medical data into predicted biophysical parameters. The mechanisms further include a generative machine learning model that is trained by the receiving of error signals from a coupling of the secondary and tertiary models, the error indicative of how well the input patient data has been transformed into predicted biophysical parameters, which when used to parameterize a biophysical model, i.e. the mechanistic model which is then represented by the surrogate machine learning model, produce outputs that are coherent with distributions of patient data and consistent with the input candidate medical data, features, reports, outcomes, diagnoses, prognoses, or progression states.

In some illustrative embodiments, an assessment component assigns a score to the biophysical model's ability to represent patient pathophysiology based on a measure of trainability of the tertiary machine learning model. The scoring of biophysical model may be performed from a comparison of the accuracy of predictions between the hybrid model and pure statistical/IL models. In some illustrative embodiments, the relevance of the input medical data is assigned a score based on the trainability of the tertiary machine learning model.

In some illustrative embodiments, the biophysical model, i.e. the surrogate ML model, is parameterized by the outputs of the tertiary machine learning model. The outputs of the biophysical model, or surrogate MT model, are visualized on a computing system, and presented to a user in order to illustrate the most likely underlying pathophysiological cause of the input patient data. The pathophysiological cause of the data is derived from informative biomarkers or clinical indices calculated from the parameters of the mechanistic model, which may be represented as the machine learning surrogate model as discussed previously and the internal hidden layer information used to provide the hidden pathophysiological information for determining the underlying pathophysiological causes of the patient data.

In some illustrative embodiments, a user may input perturbations to the parameters of the hybrid model in order to simulate "what if" scenarios relating to mechanistic model parameters. For example, a user may input perturbations to input patient data, such as one or more of the following perturbations: a comorbidity, a drug, an implanted device, an electromagnetic field, a disease progression transition, and a change in patient age. In such a case, the generative machine learning model may operate to select relevant ranges of biophysical model parameters to simulate and use as training inputs to the surrogate machine learning model. In some illustrative embodiment, the training of the surrogate ML model comprises a combination of optimization and deep learning.

In some illustrative embodiments, these perturbations to the hybrid model may be selected in order to perform predictive enrichment of a clinical trial. That is, as noted above, the hybrid architecture of the illustrative embodiments receives patient data and predicts the underlying pathophysiological parameters of a mechanistic model that are coherent with the patient data. Thus, the illustrative embodiments provide mechanisms for prediction which can be used to segment a patient population usefully in a pharmaceutical clinical trial. In simplest terms, two patients exhibiting features A1, and A2 (see FIG. 3) are associated with samples of model parameters X1, X2, and these associations predict each patient's response in the clinical trial to the drug, thereby allowing predictive enrichment (i.e., including patient 1, and excluding patient 2, from the trial, for example).

In some illustrative embodiments, the inputs to the generative machine learning model may include one or more of a wearable device signal or a medical device signal as implicitly relevant features that are used as additional inputs for the generative machine learning model training and/or generation of mechanistic model parameter samples for input to the surrogate machine learning model. Thus, during runtime operation, the inputs from such wearable and/or medical devices may be used as additional data for determination of mechanistic model parameters that are input to the surrogate ML model to generate patient features which are then used to generate predictions of patient classification.

It can be appreciated that through the training of the various machine learning models of the hybrid architecture of the illustrative embodiments, a marketplace for trained machine learning models is made possible. These machine learning models may be provided as a set of services, such that interoperable service networks may be accessed and configured in order to implement novel instantiations of the system.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for training a hybrid machine learning (ML) computer model to simulate a biophysical system of a patient and predict patient classifications based on results of simulating the biophysical system, the method comprising:
    executing a mechanistic computer model on an input dataset to generate an output dataset, wherein the input dataset and output dataset are combined to provide a training dataset for training a surrogate ML model;
    performing machine learning training of the surrogate ML model, based on the training dataset, to train the surrogate ML model to replicate logic of the mechanistic computer model as part of the surrogate ML model, and generate patient feature outputs based on surrogate ML model input parameters;
    performing machine learning training of a transformation ML model to transform patient feature outputs of the surrogate ML model into a distribution of patient features;
    performing machine learning training of a generative ML model to train the generative ML model to encode samples from a uniform distribution of input patient data into mechanistic model parameter inputs that are input to the surrogate ML model; and
    processing input patient data for a patient through the trained generative ML model, the trained surrogate ML model, and trained transformation ML model to generate a predicted patient classification for the patient, wherein training the generative ML model comprises training the generative ML model as part of an identity transformation comprising a chain of transformations comprising a first transformation, by the generative ML model, from random samples of the uniform distribution of input patient data to mechanistic model parameters, a second transformation from mechanistic model parameters input to the surrogate ML model to outputs of a mechanistic model represented as the patient feature outputs that are output by the trained surrogate ML model, and a third transformation, by the transformation ML model, from the mechanistic model outputs to observed patient features.

2. The method of claim 1, wherein training the generative ML model further comprises performing a transfer learning operation based on a loss calculation for one or more downstream ML models that are downstream in a data flow from the generative ML model to the one or more downstream ML models.

3. The method of claim 2, wherein the one or more downstream ML models comprises one or more of the surrogate ML model, the transformation ML model, or a prior ML model, wherein the prior ML model transforms a prior distribution to a uniform distribution.

4. The method of claim 2, wherein the loss calculation for the one or more downstream ML models comprises a uniformity test based loss calculation on output of the one or more downstream ML models.

5. The method of claim 2, wherein the loss calculation for the one or more downstream ML models comprises a first loss calculation for the transformation ML model and a second loss calculation for a prior ML model, wherein the generative ML model is trained to encode samples based on both the first loss calculation and the second loss calculation.

6. The method of claim 1, wherein the surrogate ML model comprises one or more hidden layers of neurons that learn hidden patient pathophysiological states that are not able to be measured non-invasively.

7. The method of claim 6, wherein the hidden patient pathophysiological states are represented in the surrogate ML model as one or more of indices or biomarkers calculated as functions of mechanistic model parameters.

8. The method of claim 1, wherein the surrogate ML model models a mechanistic biological system of the patient.

9. The method of claim 1, wherein the surrogate ML model models a cardiac system of the patient and wherein the surrogate ML model input parameters that are input to the surrogate ML model comprise heart geometry parameters of the patient.

10. A computer program product comprising a computer readable storage medium having a computer readable program stored therein, wherein the computer readable program, when executed on a computing device, causes the computing device to:
    execute a mechanistic computer model on an input dataset to generate an output dataset, wherein the input dataset and output dataset are combined to provide a training dataset for training a surrogate machine learning (ML) model;
    perform machine learning training of the surrogate ML model, based on the training dataset, to train the surrogate ML model to replicate logic of the mechanistic computer model as part of the surrogate ML model, and generate patient feature outputs based on surrogate ML model input parameters;
    perform machine learning training of a transformation ML model to transform patient feature outputs of the surrogate ML model into a distribution of patient features;
    perform machine learning training of a generative ML model to train the generative ML model to encode samples from a uniform distribution of input patient data into mechanistic model parameter inputs that are input to the surrogate ML model; and
    process input patient data for a patient through the trained generative ML model, the trained surrogate ML model, and trained transformation ML model to generate a predicted patient classification for the patient, wherein training the generative ML model comprises training the generative ML model as part of an identity transformation comprising a chain of transformations comprising a first transformation, by the generative ML model, from random samples of the uniform distribution of input patient data to mechanistic model parameters, a second transformation from mechanistic model parameters input to the surrogate ML model to outputs of a mechanistic model represented as the patient feature outputs that are output by the trained surrogate ML model, and a third transformation, by the transformation ML model, from the mechanistic model outputs to observed patient features.

11. The computer program product of claim 10, wherein training the generative ML model further comprises performing a transfer learning operation based on a loss calculation for one or more downstream ML models that are downstream in a data flow from the generative ML model to the one or more downstream ML models.

12. The computer program product of claim 11, wherein the one or more downstream ML models comprises one or more of the surrogate ML model, the transformation ML model, or a prior ML model, wherein the prior ML model transforms a prior distribution to a uniform distribution.

13. The computer program product of claim 11, wherein the loss calculation for the one or more downstream ML models comprises a uniformity test based loss calculation on output of the one or more downstream ML models.

14. The computer program product of claim 11, wherein the loss calculation for the one or more downstream ML models comprises a first loss calculation for the transformation ML model and a second loss calculation for a ML model, wherein the generative ML model is trained to encode samples based on both the first loss calculation and the second loss calculation.

15. The computer program product of claim 10, wherein the surrogate ML model comprises one or more hidden layers of neurons that learn hidden patient pathophysiological states that are not able to be measured non-invasively.

16. The computer program product of claim 15, wherein the hidden patient pathophysiological states are represented in the surrogate ML model as one or more of indices or biomarkers calculated as functions of mechanistic model parameters.

17. The computer program product of claim 10, wherein the surrogate ML model models a mechanistic biological system of the patient.

18. An apparatus comprising:
a processor; and
a memory coupled to the processor, wherein the memory comprises instructions which, when executed by the processor, cause the processor to:
execute a mechanistic computer model on an input dataset to generate an output dataset, wherein the input dataset and output dataset are combined to provide a training dataset for training a surrogate machine learning (ML) model;
perform machine learning training of the surrogate ML model, based on the training dataset, to train the surrogate ML model to replicate logic of the mechanistic computer model as part of the surrogate ML model, and generate patient feature outputs based on surrogate ML model input parameters;
perform machine learning training of a transformation ML model to transform patient feature outputs of the surrogate ML model into a distribution of patient features;
perform machine learning training of a generative ML model to train the generative ML model to encode samples from a uniform distribution of input patient data into mechanistic model parameter inputs that are input to the surrogate ML model; and
process input patient data for a patient through the trained generative ML model, the trained surrogate ML model, and trained transformation ML model to generate a predicted patient classification for the patient, wherein training the generative ML model comprises training the generative ML model as part of an identity transformation comprising a chain of transformations comprising a first transformation, by the generative ML model, from random samples of the uniform distribution of input patient data to mechanistic model parameters, a second transformation from mechanistic model parameters input to the surrogate ML model to outputs of a mechanistic model represented as the patient feature outputs that are output by the trained surrogate ML model, and a third transformation, by the transformation ML model, from the mechanistic model outputs to observed patient features.

* * * * *